(12) United States Patent
Knutsson

(10) Patent No.: US 11,324,928 B2
(45) Date of Patent: May 10, 2022

(54) NEEDLE ASSEMBLY

(71) Applicant: Vigmed AB, Helsingborg (SE)

(72) Inventor: Per Knutsson, Helsingborg (SE)

(73) Assignee: Greiner Bio-One GmbH, Kremsmunster (AT)

( * ) Notice: Subject to any disclaimer, the term of this patent is extended or adjusted under 35 U.S.C. 154(b) by 0 days.

(21) Appl. No.: 14/766,094

(22) PCT Filed: Feb. 4, 2014

(86) PCT No.: PCT/SE2014/050138
§ 371 (c)(1),
(2) Date: Aug. 5, 2015

(87) PCT Pub. No.: WO2014/123475
PCT Pub. Date: Aug. 14, 2014

(65) Prior Publication Data
US 2015/0367104 A1     Dec. 24, 2015

(30) Foreign Application Priority Data

Feb. 5, 2013   (SE) .................................... 1350137-4

(51) Int. Cl.
*A61M 25/06*    (2006.01)
*A61B 5/15*     (2006.01)
(Continued)

(52) U.S. Cl.
CPC ......... *A61M 25/0637* (2013.01); *A61B 5/153* (2013.01); *A61B 5/15003* (2013.01);
(Continued)

(58) Field of Classification Search
CPC .............. A61M 25/02; A61M 25/0618; A61M 5/3216; A61M 25/0631; A61M 25/0637;
(Continued)

(56) References Cited

U.S. PATENT DOCUMENTS 4,664,655 A    5/1987   Orentreich et al.
4,820,277 A *  4/1989   Norelli ................ A61M 5/3216
                                                          604/192

(Continued)

FOREIGN PATENT DOCUMENTS

CN          1406640         4/2003
CN          1446516 A      10/2003
(Continued)

OTHER PUBLICATIONS

Bibliographic Data Sheet indicating Abstract not available for SE1150633(A1), dated Jan. 6, 2013.
(Continued)

*Primary Examiner* — Scott J Medway
(74) *Attorney, Agent, or Firm* — Fishman Stewart PLLC

(57) ABSTRACT

A needle assembly for percutaneously infusing fluids to a body and/or withdrawing fluids from a body is provided. The needle assembly comprises a polymeric body having a passageway in a proximodistal direction. A wing assembly is secured to the body, and the wing assembly including first and second wings extending laterally in opposite directions from said body. A hollow needle is arranged in said passageway, such that it extends distally from said body, wherein said needle is press fitted or interference fitted in said passageway.

20 Claims, 3 Drawing Sheets

(51) Int. Cl.
*A61M 5/32* (2006.01)
*A61M 25/02* (2006.01)
*A61B 5/153* (2006.01)
*A61M 5/158* (2006.01)

(52) U.S. Cl.
CPC .... *A61B 5/15074* (2013.01); *A61B 5/150389* (2013.01); *A61B 5/150503* (2013.01); *A61B 5/150679* (2013.01); *A61M 5/158* (2013.01); *A61M 5/3216* (2013.01); *A61M 25/02* (2013.01); *A61M 25/0618* (2013.01); *A61M 25/0631* (2013.01); *A61M 2005/3217* (2013.01); *A61M 2205/6081* (2013.01)

(58) Field of Classification Search
CPC ...... A61M 25/3217; A61M 2205/6081; A61M 2005/1585; A61M 25/0606; A61B 5/153; A61B 5/15003; A61B 5/150389; A61B 5/150503; A61B 5/150679
USPC ..... 604/164.08, 165.03, 171, 177, 198, 263, 604/272
See application file for complete search history.

(56) References Cited

U.S. PATENT DOCUMENTS

| | | | |
|---|---|---|---|
| 4,888,001 A | 12/1989 | Schoenberg | |
| 4,941,881 A * | 7/1990 | Masters | A61M 25/0637 604/162 |
| 4,982,842 A * | 1/1991 | Hollister | A61M 5/3216 206/365 |
| 5,088,982 A * | 2/1992 | Ryan | A61M 5/3243 600/576 |
| 5,093,967 A * | 3/1992 | Frank | A41H 37/001 24/693 |
| 5,151,089 A * | 9/1992 | Kirk, III | A61M 5/3216 604/192 |
| 5,169,391 A * | 12/1992 | Vogel | A61M 5/3213 604/177 |
| 5,188,611 A * | 2/1993 | Orgain | A61M 5/3216 604/192 |
| 5,242,417 A | 9/1993 | Paudler | |
| 5,266,072 A * | 11/1993 | Utterberg | A61M 25/0637 604/177 |
| 5,290,264 A * | 3/1994 | Utterberg | A61M 25/0637 604/174 |
| 5,312,368 A * | 5/1994 | Haynes | A61M 5/3216 604/192 |
| 5,312,369 A * | 5/1994 | Arcusin | A61M 5/3216 604/192 |
| 5,405,332 A * | 4/1995 | Opalek | A61M 5/3216 604/192 |
| 5,490,841 A * | 2/1996 | Landis | A61M 5/3216 128/919 |
| 5,599,313 A * | 2/1997 | Gyure | A61M 5/3216 604/111 |
| 5,643,219 A * | 7/1997 | Burns | A61M 5/3216 604/192 |
| 5,669,889 A * | 9/1997 | Gyure | A61M 5/3216 604/263 |
| 5,674,201 A * | 10/1997 | Steinman | A61M 25/02 604/165.03 |
| 5,681,295 A * | 10/1997 | Gyure | A61M 5/3202 604/263 |
| 5,693,022 A * | 12/1997 | Haynes | A61M 5/3216 604/192 |
| 5,733,265 A * | 3/1998 | Bachman | A61M 5/3216 604/192 |
| 5,931,815 A * | 8/1999 | Liu | A61M 25/0631 604/171 |
| 6,059,758 A * | 5/2000 | Padilla | A61M 5/3213 604/192 |
| RE37,110 E * | 3/2001 | Hollister | A61M 5/3216 206/365 |
| 6,413,243 B1 * | 7/2002 | Geist | A61M 5/3216 604/110 |
| 6,440,104 B1 | 8/2002 | Newby et al. | |
| 6,623,461 B1 * | 9/2003 | Wilkinson | A61M 5/3243 604/177 |
| 6,699,217 B2 * | 3/2004 | Bennett | A61M 5/3216 128/919 |
| 6,773,419 B2 * | 8/2004 | Crawford | A61B 5/15003 600/576 |
| 6,881,202 B2 * | 4/2005 | Coleman | A61M 5/158 604/165.03 |
| 6,974,444 B2 * | 12/2005 | Von Teichert | A61M 5/3243 128/919 |
| 7,112,190 B2 * | 9/2006 | Bressler | A61M 25/0631 604/263 |
| 7,294,118 B2 * | 11/2007 | Saulenas | A61M 25/0631 604/110 |
| 7,682,339 B2 * | 3/2010 | Fujii | A61M 25/0606 604/164.08 |
| 7,691,083 B2 * | 4/2010 | Botich | A61B 5/150572 604/110 |
| 7,776,016 B1 * | 8/2010 | Halseth | A61M 5/158 604/162 |
| 7,776,018 B2 * | 8/2010 | Bush, Jr. | A61M 5/32 285/345 |
| 8,038,654 B2 * | 10/2011 | Lim | A61M 5/3216 604/192 |
| 8,192,404 B2 * | 6/2012 | Murashita | A61M 5/158 604/167.01 |
| 8,439,838 B2 * | 5/2013 | Mogensen | A61B 5/14532 600/365 |
| 8,574,197 B2 * | 11/2013 | Halseth | A61M 5/158 604/162 |
| 8,641,680 B2 * | 2/2014 | Simas, Jr. | A61M 5/3216 604/198 |
| 8,888,713 B2 * | 11/2014 | Crawford | A61B 5/1422 600/576 |
| 9,259,533 B2 * | 2/2016 | Weilbacher | A61M 5/158 |
| 2001/0008963 A1 | 7/2001 | Alesi | |
| 2002/0099342 A1 * | 7/2002 | Zurcher | A61M 25/0631 604/272 |
| 2003/0199827 A1 * | 10/2003 | Thorne | A61M 25/0631 604/164.08 |
| 2004/0087912 A1 | 5/2004 | Swenson | |
| 2005/0065482 A1 * | 3/2005 | Hauri | A61M 5/3202 604/263 |
| 2005/0107748 A1 | 5/2005 | Thorne et al. | |
| 2005/0119635 A1 | 6/2005 | Crawford | |
| 2005/0124944 A1 * | 6/2005 | Hwang | A61M 5/3216 604/263 |
| 2006/0074387 A1 * | 4/2006 | Thorne | A61M 5/158 604/263 |
| 2006/0264778 A1 * | 11/2006 | Lim | A61B 5/417 600/576 |
| 2007/0100296 A1 * | 5/2007 | Hwang | A61M 5/3275 604/263 |
| 2007/0250011 A1 * | 10/2007 | Lee | A61M 25/0606 604/165.03 |
| 2008/0208138 A1 * | 8/2008 | Lim | A61M 5/3216 604/192 |
| 2012/0016307 A1 | 1/2012 | Burkholz et al. | |
| 2015/0367104 A1 * | 12/2015 | Knutsson | A61M 25/02 604/177 |

FOREIGN PATENT DOCUMENTS

| | | | |
|---|---|---|---|
| CN | 1520893 A | 8/2004 | |
| CN | 101687083 A | 3/2010 | |
| EP | 0815889 A2 * | 1/1998 | ......... A61M 5/3216 |
| EP | 0819441 A1 * | 1/1998 | ......... A61M 5/3216 |
| EP | 0827754 A1 * | 3/1998 | ......... A61M 5/3216 |
| EP | 1030597 A1 | 8/2000 | |
| EP | 1537890 A1 | 6/2005 | |
| EP | 1941924 A1 | 7/2008 | |

(56) References Cited

FOREIGN PATENT DOCUMENTS

| | | |
|---|---|---|
| JP | 1984-18986 | 12/1989 |
| JP | 1996-257130 | 4/1997 |
| JP | 2003-310757 A | 11/2003 |
| SE | 1150633 A1 | 1/2013 |
| WO | WO-2004/032995 A2 | 4/2004 |
| WO | WO-2005/105195 A1 | 11/2005 |
| WO | WO-2011/085239 A1 | 7/2011 |
| WO | WO-2013/006134 A1 | 1/2013 |

OTHER PUBLICATIONS

Pre-Appeal Report for Japanese Patent Application No. 2015-555965.
European Search Report Issued for European Patent Application No. 14749264.9 dated Mar. 20, 2020.
Chinese Search Report dated Jul. 17, 2021 related to corresponding Chinese Patent Application No. 201911316567.9.
Chinese Office Action dated Jul. 23, 2021 related to corresponding Chinese Patent Application No. 201911316567.9.
European Communication Pursuant to Article 94(3) EPC for European Patent Application No. 14 749 264.9 dated May 27, 2021.
Japanese Office Action dated Aug. 2, 2016 for Japanese Patent Application No. 2015-555965.

\* cited by examiner

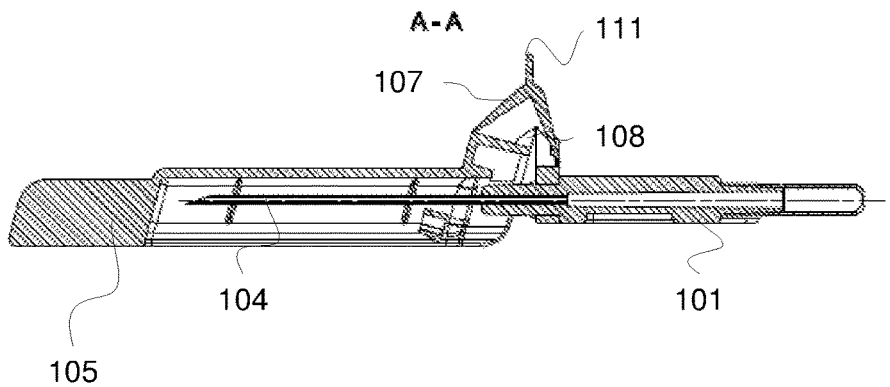
Fig. 5
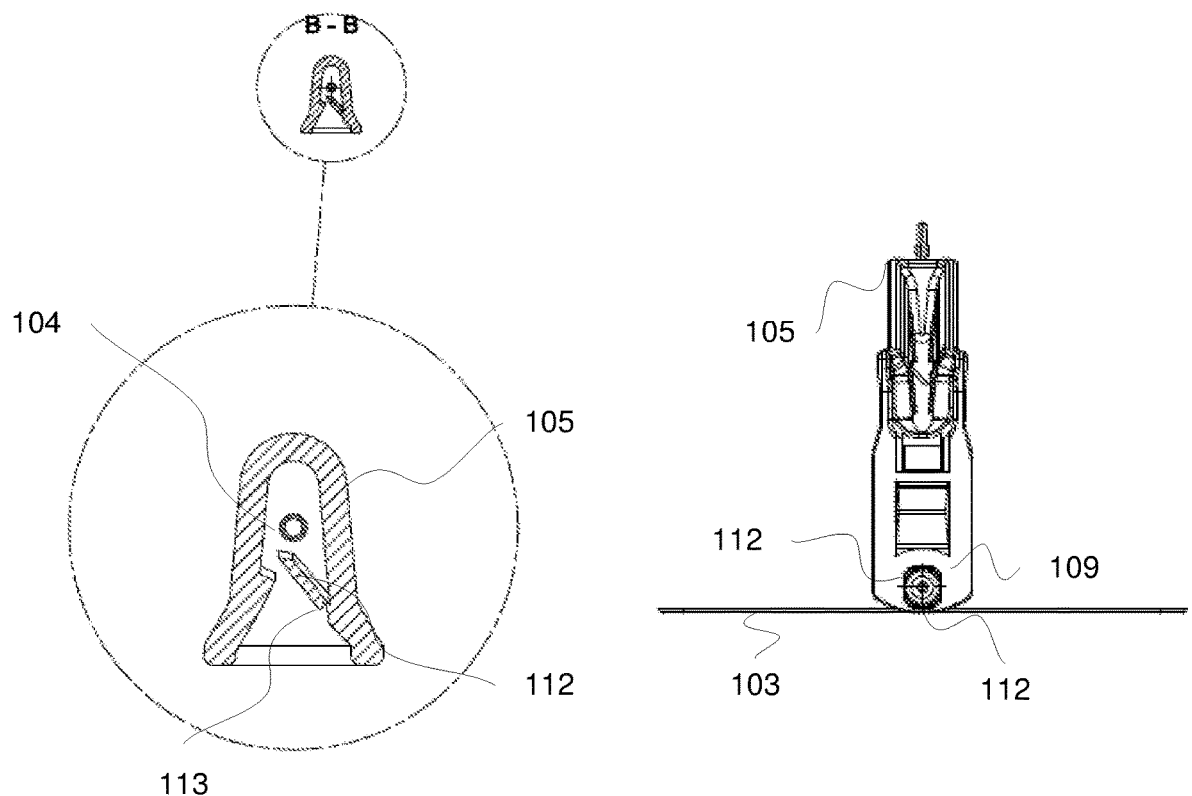
Fig. 6
Fig. 7

NEEDLE ASSEMBLY

CROSS-REFERENCE TO RELATED APPLICATIONS

This application is a U.S. National phase based on PCT/SE2014/050138, filed on Feb. 4, 2014 entitled "NEEDLE ASSEMBLY" which is based on Swedish Patent Application No. 1350137-4, filed on Feb. 5, 2013, each of which is hereby incorporated by reference in its entirety.

TECHNICAL FIELD

The present disclosure pertains to an apparatus and methods for percutaneously infusing fluids to a body and/or withdrawing fluids from a body. More precisely, the present disclosure pertains to a needle assembly for percutaneously infusing fluids to a body and/or withdrawing fluids from a body, comprising a body having a passageway in a proximodistal direction, and a wing assembly secured to the body, the wing assembly including first and second wings extending laterally in opposite directions from said body, and a hollow needle arranged in said passageway, such that it extends distally from said body.

BACKGROUND

Needle assemblies are commonly used to percutaneously infuse fluids to a body and/or withdraw fluids from a body. The needle assembly generally remains disposed in the vasculature while one or more assemblies are connected and disconnected to the assembly to complete the infusion/withdrawal process. To facilitate insertion and attachment of the needle assembly to the skin of the patient, the needle assembly is provided with wings. The wings are, during insertion of the needle assembly folded upwards, to allow for a smooth grip of the needle assembly during insertion. After insertion, the wings are flexing back to their resting state, in which they extend laterally. In this position, the wings will be arranged adjacent and parallel to the skin of the patient, wherein the needle assembly may be fixed to the skin of the patient through taping over the wings. Then, the needle assembly may be secured to the skin of the patient, preventing axial, transversal and rotational movement, which could create undue discomfort or even hurt the patient.

To allow for these functions, which demands for an amount of flexibility, the wings are made of a suitable elastomer. Due to the flexibility of the elastomeric material, the needle is then glued to wings, either directly or via an intermediate body. This step of gluing adds a manufacturing step, which in turn adds on manufacturing costs.

Also, upon withdrawing the needle assembly from the vasculature, the sharp distal tip of the needle is exposed. It is disadvantageous to leave the tip exposed, as there is a risk that medical staff can accidentally prick themselves. This phenomenon is know as needlestick, and can transfer blood borne diseases, such as hepatitis and HIV.

Systems have been suggested, wherein a slidable tube is slid distally over the needle after withdrawal of the needle. Alternatively, a shielding arm may be pivoted over the needle tip. However, due to the high elasticity of the elastomeric body and wings, the shielding arm has to be adhered proximally of the wings after the needle has been glued, since the needle needs to be present to obtain satisfactory stability for adherence of the shielding arm and distal arrangement means undue precision work over the needle during gluing, making it incompatible with industrial manufacturing, since the risk of glue contacting the needle is too high. This adds unnecessary length to the product when the arm is pivoted proximally, such as in packaged and transportation state. Still further, both of these systems provide a safety alternative wherein the safety mechanism has to be activated after use. This means that there is still a risk of needlestick during activation of the safety mechanism or if the patient twitches or moves rapidly, such that the needle assembly unintentionally is withdrawn from vasculature.

Hence, a new winged needle assembly would be beneficial, and especially a winged needle assembly allowing for decreased manufacturing costs, decreased storing and transportation volume, and provision of a safety mechanism that can be activated prior to or while introducing the needle assembly into the vasculature of a patient.

SUMMARY

It is an object of the present disclosure, considering the disadvantages mentioned above, to provide a needle assembly overcoming at least some of the drawbacks mentioned above, which has been achieved by a needle assembly for percutaneously infusing fluids to a body and/or withdrawing fluids from a body, comprising: a polymeric body having a passageway in a proximodistal direction; a wing assembly secured to the body, the wing assembly including first and second wings extending laterally in opposite directions from said body; and a hollow needle arranged in said passageway, such that it extends distally from said body; wherein said needle is press fitted/interference fitted in said passageway.

Further features of the disclosure and its embodiments are set forth in the appended claims.

BRIEF DESCRIPTION OF THE DRAWINGS

These and other aspects, features and advantages of which the disclosure is capable will be apparent and elucidated from the following description of non-limiting embodiments of the present disclosure, reference being made to the accompanying drawings, in which

FIG. 5 is a cross sectional view, along the longitudinal axis, of one embodiment of the present disclosure in closed position;

FIG. 6 is a cross sectional view, in the transverse plane, of one embodiment of the present disclosure in closed position; and FIG. 7 is a front view of one embodiment of the present disclosure in open position.

DETAILED DESCRIPTION OF THE EMBODIMENTS

Embodiments of the present disclosure will be described in more detail below with reference to the accompanying drawings in order for those skilled in the art to be able to carry out the disclosure. The disclosure may, however, be embodied in many different forms and should not be construed as limited to the embodiments set forth herein. Rather, these embodiments are provided so that this disclosure will be thorough and complete, and will fully convey the scope of the disclosure to those skilled in the art.

Furthermore, the terminology used in the detailed description of the particular embodiments illustrated in the accompanying drawings is not intended to be limiting of the disclosure. More specifically, the term "proximal" refers to a location or direction of items or parts of items, during normal use of the needle assembly system disclosed herein, that is closest to the user, i.e. the clinician, and farthest away from the patient receiving the needle assembly. Similarly, the term "distal" refers to a location or direction of items or parts of items, during normal use of the needle assembly disclosed herein, that is closest to the patient and farthest away from the clinician. The term "laterally" refers to the direction away from the central axis of the needle assembly, such that at least a vector component perpendicular to the central axis of the needle assembly.

Figure 1:
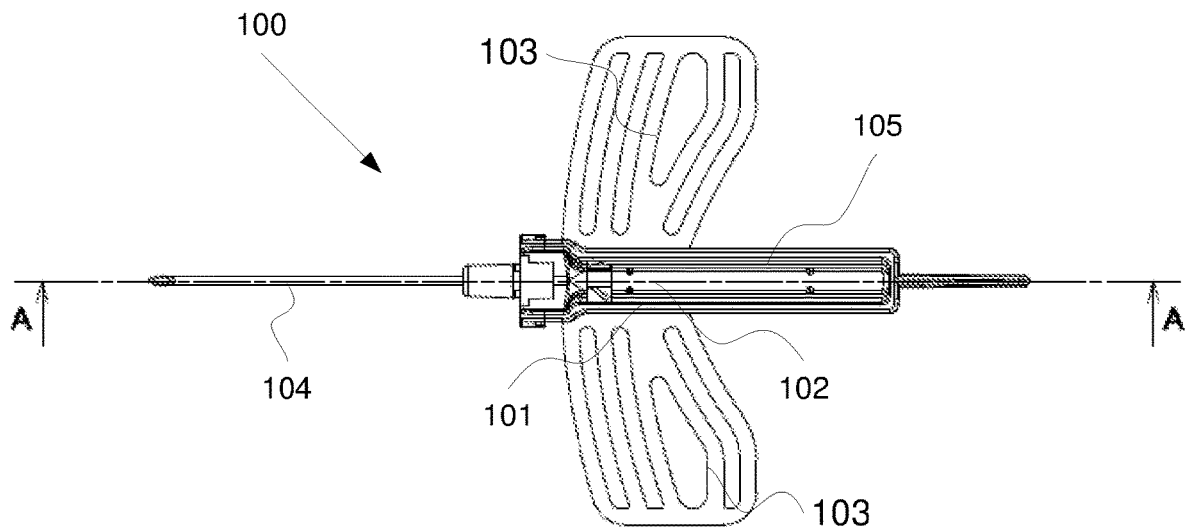
FIG. 1 is a top view of one embodiment of the present disclosure in open position.
Figure 2:
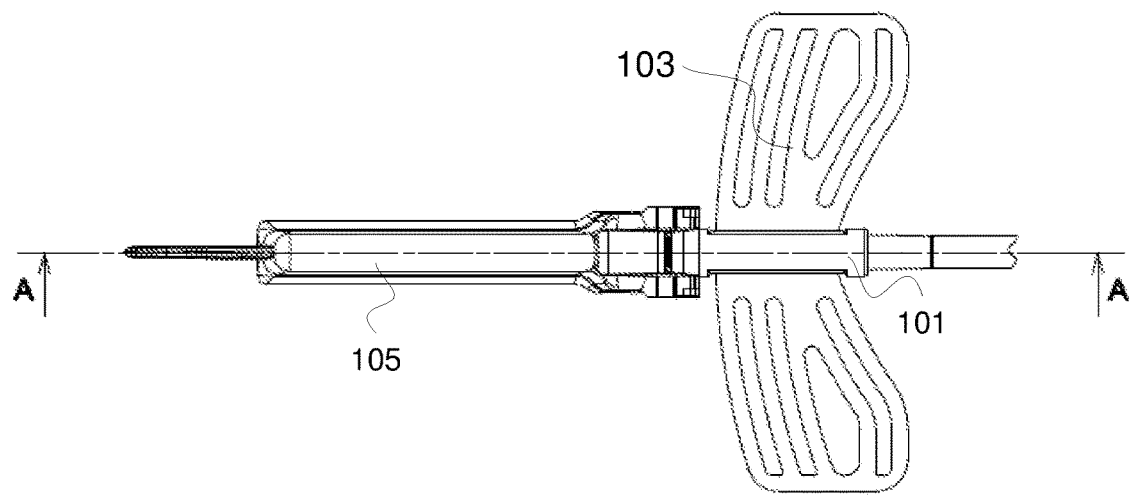
FIG. 2 is a top view of one embodiment of the present disclosure in closed position.
Figure 3:
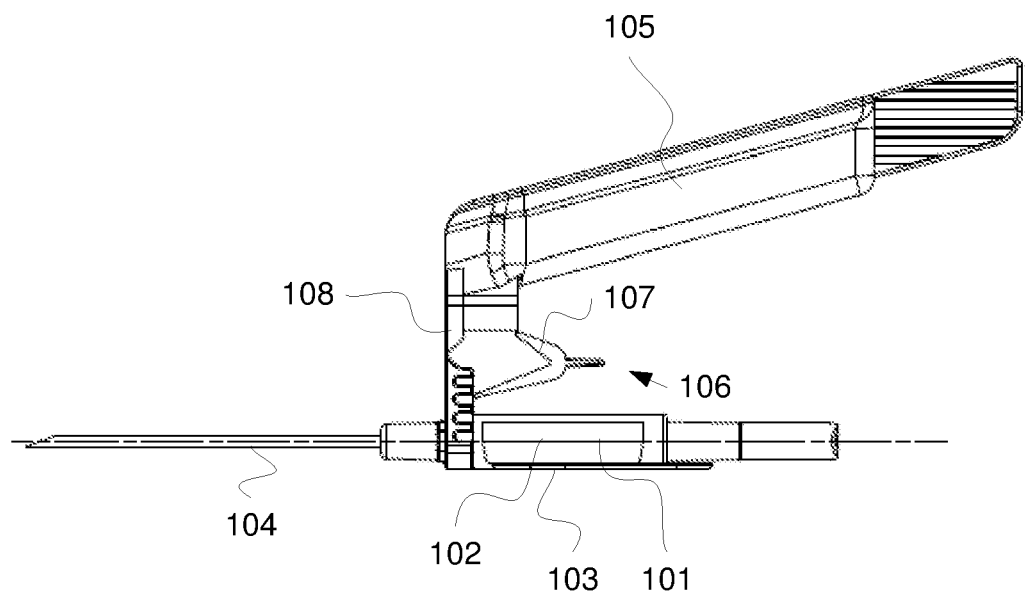
FIG. 3 is a side view of one embodiment of the present disclosure in open position.
Figure 4:
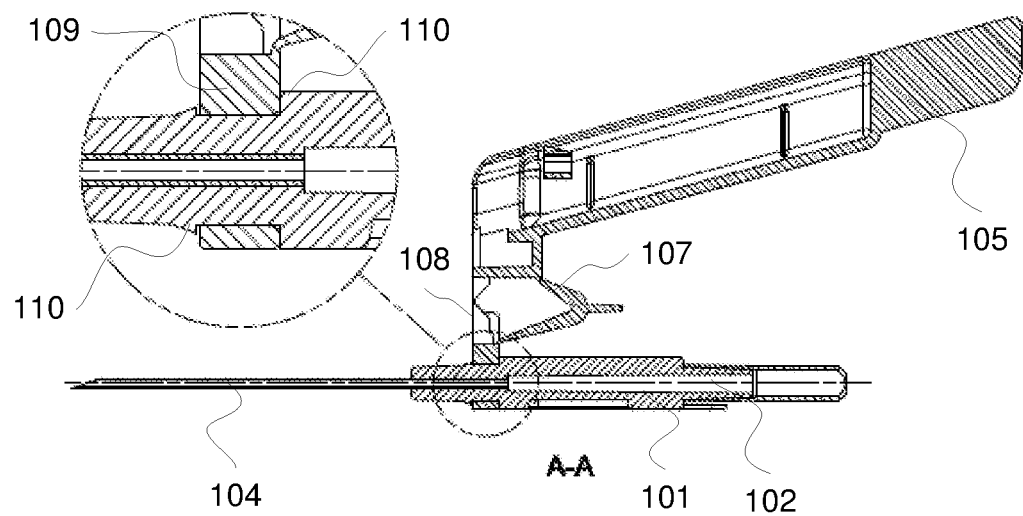
FIG. 4 is a cross sectional view, along the longitudinal axis, of one embodiment of the present disclosure in open position.

A needle assembly 100, according to one embodiment of the present disclosure, is disclosed in FIGS. 1 to 6. The needle assembly 100 is adapted and intended for percutaneously infusing fluids to a body and/or withdrawing fluids from a body. The needle assembly 100 comprises a body 101. The body 101 is a polymeric body.

The polymeric material of the body 101 may be selected from the group comprising thermoplastic materials, such as polyolefins, such as polypropylene, polyethylene, copolymers of these, or copolymers of these two. These materials will allow for press or interference fitting of the needle 104 in the lumen/passageway 102 to a degree ensuring that the needle 104 will be retained in the body 101 also during and after use.

The body 101 comprises a lumen in the proximodistal direction, i.e. a passageway 102. A wing assembly is secured to the body 101. The wing assembly includes a first and a second wing 103. The wings 103 extend laterally in opposite directions from said body 101. The thickness of the wings 103 is selected to be below 0.50 mm, such from 0.15 to 0.35 mm, to provide flexibility similar to elastomeric wings. In one embodiment the wings 103 may be provided with a longitudinal groove, in which groove the wings 103 has a thickness below 0.50 mm, such from 0.15 to 0.35 mm. Then, at least, the wings may be folded in resemblance with elastomeric wings even if the rest of the wings 103 not will have flexibility like the one obtained below 0.50 mm.

The body 101 and the wings 103 may be manufactured as one monolithic body, for example through injection molding these parts together. Thus, also the wings 103 may be made of a material selected from the group comprising polypropylene, polyethylene, copolymers of these, or copolymers of these two. Since the flexibility of the wings 103 are of great importance, since the wings preferably should be able to be folded upwardly prior to insertion of the needle into the vasculature, at has hitherto been thought that only elastomers could be used for this purpose. However, by providing the wings with cut-outs or tracks, and injection molding the wings sufficiently thin, the wings 103 may get flexibility characteristics similar to elastomers. Thus, a monolithic body/wing assembly may be obtained which eliminates the use of a gluing step during the manufacturing, since it has been surprisingly been envisioned that the wings may be manufactured in a material that is also suitable for press/interference fitting with the needle 104.

A hollow needle is arranged in said passageway 102, such that it extends distally from said body 101. The needle 104 is press fitted or interference fitted in said passageway 102, in accordance with above. The press fitting may be performed by dimensioning the lumen or passageway 102 to be somewhat smaller than the diameter of the needle 104 in the proximal end of the diameter, and then inserting the needle at the proximal end of the body 101. The needle 104 is then pushed into retaining cooperation with the lumen/passageway 102 of the body 101.

The needle assembly 100 may further comprise a shielding arm 105. The shielding arm 105 may be attached to the body 101 such that it is pivotable from an open position (as disclosed in FIGS. 1, 3, and 4) to a closed position (as disclosed in FIGS. 2 and 5). In the closed position the tip of the needle 104 is covered by the shielding arm 105 while the needle tip is uncovered in the open position.

The shielding arm 105 is connected to the body 101 in a position distally of the wing assembly, i.e. the wings 103. This may be accomplished since the needle 104 may be press/interference fitted with the body 101. Hence, the needle 104 may be connected to the body 101 after arranging the shielding arm 105 on the body 101. This would not be possible with an elastomeric body, since such a body would need the needle to be glued to the body, whereby the shielding arm would have to be connected to the body proximally of the wings, thus adding unnecessary product length in open position, making the product impractical to store and insert into the vasculature.

The shielding arm 105 is connected to the body 101 via a hinge structure 106, for urging said shielding arm 105 into one of either said open position or said closed position. The hinge structure 106 has a dead-center position, such that said shielding arm 105 is urged into said open position and said closed position, respectively, on corresponding sides of said dead-center position. To accomplish this, the needle assembly 100 may, for example, comprise a hinge structure 106 comprising at least one toggle joint 107 and at least one tension member 108. The at least one toggle joint 107 and at least one tension member 108 may be connected to said shielding arm 105 via a mounting base 109, which in turn is connected to the body 101.

It is however also envisioned that the arm 105, comprising the hinge structure 106, may be injection molded together with the body 101, and also possibly with the wing assembly, into a monolithic piece, since also the arm 105 may be provided with suitable spring characteristics, through the use of a toggle joint 107 and a tension member 108, in the materials disclosed above, such as polypropylene, polyethylene, copolymers of these, or copolymers of these two.

The mounting base 109 may be ring-shaped, and may be connected to the body 101 through snap-fitting the ring-shaped mounting base 109 into a reception groove on the body 101. For this purpose, the body 101 may be provided with heels 110, over which the ring-shaped mounting base 109 may be snap fitted. These heels 110 or the reception groove will prevent the mounting base 109, and consequently also the arm 105 from axial movement in relation to the body 101, and thus also the needle 104, being in fixed relationship with the body 101 through the press/interference fitting thereof.

To prevent rotational movement of the mounting base 109, and thus also the arm 105, the ring-shaped mounting base 109 may be provided with an axial groove or ridge, which may cooperate with a corresponding ridge or groove, respectively, on the body 101. Also, the transversal cross section of the part of body 101 intended to receive the mounting base 109 may be polygonal, such as square, or at least provided with a cut plane, such as two cut planes, such as disclosed in FIG. 7. When the mounting base 109 is fitted circumferentially of a body 101 with a receiving portion of this kind, the mounting base, and thus the arm 105, is prevented from rotational movement in relation to the body 101.

The dead-center position may be arranged such that the angle between the longitudinal extension of said needle 104 and the longitudinal extension of said shielding arm 105 is in the range of 45 to 135° in said dead-center position, when said mounting base 109 is attached to or monolithic with said body 101.

The needle assembly 100 may be provided with an actuator tab 111 at the knee of the toggle joint 107. This actuator tab 111 then extends outwardly, as an extension of, the toggle joint 107, such that actuation, i.e. transformation from open to closed position of the shielding arm 105, may be facilitated.

The shielding arm 105 may be provided with a locking bar 112, extending transversally of said shielding arm 105. The shielding arm 105, when releasing the spring loaded hinge structure 106, such that the arm 105 is urged towards the closed position, will make the arm 105 to be forced towards the needle 104. The locking bar 112 will then be surpassed by the needle 104 by the spring force in hinge structure 106. The locking bar 112 may be provided with a slit 113 on the outside of the bar 112, to facilitate needle movement beyond the bar 112, but simultaneously preventing the needle 104 from moving in the opposite direction.

In FIG. 7, the body 101 has a square transversal cross section of the part of body 101 intended to receive the mounting base 109, i.e. with four cut planes 114, onto which the mounting base 109 is arranged.

For allowing a good fit between the needle 104 and the body 101 and also a good spring effect of the arm 105, the polymeric material may be selected such that the molded article will have a Young's modules (tensile modulus or elastic modulus) in the range of 500 MPa to 2000 MPa. In this interval the plastic material will satisfy both needs, regardless of the body 101 and the arm 105 are manufactured as one monolithic body or not—both alternatives being readily understood to be within the ambit of the present disclosure.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A needle assembly for percutaneously infusing fluids, comprising:
   a polymeric body having a passageway, and an outer surface, the outer surface of the polymeric body having a circumferentially continuous, outwardly tapering protrusion located at a distal end of the body, the body further including a first heel and a second heel with a reception groove located in between the first and second heels, the reception groove is formed on the polymeric body and the groove is operable to receive a mounting base;
   a wing assembly secured to the polymeric body, the wing assembly including first and second wing extending laterally in opposite directions from said polymeric body;
   a hollow needle arranged in said passageway, such that it extends distally from said polymeric body; and
   a mounting base including a ring structure having a length configured to snap fit into the reception groove of the outer surface of the polymeric body in response to being positioned over the circumferentially continuous, outwardly tapering protrusion and into the reception groove;
   wherein the reception groove is positioned distally of the wing assembly,
   wherein said needle is press fitted or interference fitted in said passageway, the polymeric body and the wing assembly are comprised in one monolithic unit; and
   a hinge structure is configured to permit an arm to pivot relative to the polymeric body, the hinge structure including at least one toggle joint and at least one tension member.

2. The needle assembly according to claim 1, wherein the polymeric body is manufactured of a thermoplastic material; and
   wherein the reception groove includes opposing sidewalls adjacent to the outwardly tapering protrusion, and the mounting base includes radially extending distal and proximal walls that are configured to be positioned between the opposing sidewalls of the reception groove.

3. The needle assembly according to claim 1, wherein the first and second wings are manufactured of a thermoplastic material.

4. The needle assembly according to claim 2, wherein the thermoplastic material of the polymeric body is selected from the group consisting of polypropylene or a copolymer.

5. The needle assembly according to claim 1, wherein the polymeric body and the wing assembly are comprised in one monolithic unit.

6. The needle assembly according to claim 1, further comprising a shielding arm being attached to the polymeric body, such that it is pivotable from an open position to a closed position, wherein a tip of the needle is covered by the shielding arm in the closed position while the needle tip is uncovered in the open position.

7. The needle assembly according to claim 6, wherein the ring groove of the polymeric body is configured with a polygon shape to prevent rotational motion of the body.

8. The needle assembly according to claim 7, wherein said hinge structure has a central position, such that said shielding arm is urged into said open position and said closed position, respectively, on corresponding sides of said central position.

9. The needle assembly according to claim 1, said at least one toggle joint and at least one tension member being connected to a shielding arm and said mounting base.

10. The needle assembly according to claim 1, wherein said mounting base is a separate item arranged and retained on said polymeric body.

11. The needle assembly according to claim 1, wherein said heels are configured to prevent said mounting base from axially moving relative to said polymeric body.

12. The needle assembly according to claim 8, wherein said central position is a position in which the angle between the longitudinal extension of said needle and the longitudinal extension of said shielding arm is in the range of 45 to 135°, when said mounting base is attached to or monolithic with said polymeric body.

13. The needle assembly according to claim 8, wherein said shielding arm is provided with at least one needle locking bar extending transversally of said shielding arm.

14. The needle assembly according to claim 13, wherein said locking bar comprises at least one slit on an outside surface of the bar.

15. The needle assembly according to claim 7, wherein the shielding arm is attached distally of said wings.

16. A needle assembly for percutaneously infusing fluids, comprising:
   a polymeric body having a passageway and an outer surface, the outer surface of the polymeric body having a circumferentially continuous, outwardly tapering protrusion, an outer diameter portion, and a smaller diameter portion, the smaller diameter portion is positioned between the tapering protrusion and the outer diameter portion, the smaller diameter portion is formed on the body to provide a reception groove for receiving a mounting base;
   a wing assembly secured to the polymeric body, the wing assembly including first and second wings extending laterally in opposite directions from said polymeric body;
   a hollow needle arranged in said passageway, such that it extends distally from said polymeric body; and
   a mounting base including a ring structure having a length configured to snap fit into the reception groove;
   a hinge structure positioned between a shielding arm and the mounting base, the hinge structure including at least one toggle joint and at least one tension member; and
   wherein the reception groove is positioned distally of the wing assembly,
   wherein the polymeric body is manufactured of a thermoplastic material.

17. The needle assembly according to claim 16, wherein said thermoplastic material is a polyolefin.

18. The needle assembly according to claim 17, wherein said polyolefin is selected from the group consisting of polypropylene, polyethylene, copolymers of these, or copolymers of these two.

19. A needle assembly for percutaneously infusing fluids, comprising:
   a polymeric body having a passageway and an outer surface with a first diameter, the outer surface of the polymeric body further having a circumferentially continuous, outwardly tapering protrusion and a reception groove, the reception groove is formed on the body and has an outside diameter that is less than the first diameter, the reception groove is positioned distally of a wing assembly;
   the wing assembly is secured to the polymeric body, the wing assembly including first and second wings extending laterally in opposite directions from said polymeric body;
   and a hollow needle arranged in said passageway, such that it extends distally from said polymeric body;
   a shielding arm being attached to the polymeric body, such that it is pivotable from an open position to a closed position, wherein a tip of the needle is covered by the shielding arm in the closed position while the needle tip is uncovered in the open position, the shielding arm includes a locking bar extending transversely of said arm, said locking bar includes a slit, the locking bar is configured to permit movement of a needle in one direction past the bar, but prevents a needle from moving in an opposite direction;
   a mounting base including a ring structure having a length configured to snap fit into the reception groove, the ring structure having an inside diameter that is substantially the same as the outside diameter of the reception groove; and
   a hinge structure connecting the polymeric body and the shielding arm, the hinge structure including at least one toggle joint and at least one tension member.

20. The needle assembly according to claim 19, wherein the shielding arm is attached distally of said wings.

* * * * *